United States Patent [19]
Wilk

[11] Patent Number: 5,626,590
[45] Date of Patent: May 6, 1997

[54] LAPAROSCOPIC SUTURING TECHNIQUE AND ASSOCIATED DEVICE

[76] Inventor: Peter J. Wilk, 185 W. End Ave., New York, N.Y. 10023

[21] Appl. No.: 391,237

[22] Filed: Feb. 21, 1995

Related U.S. Application Data

[63] Continuation-in-part of Ser. No. 195,749, Feb. 10, 1994, Pat. No. 5,391,173.

[51] Int. Cl.⁶ .................................................. A61B 17/04
[52] U.S. Cl. ........................ 606/148; 606/139; 606/232
[58] Field of Search .......................... 606/139, 144–148, 606/232; 24/115, 129 R, 130, 131 C, 324, 453, 129 W

[56] References Cited

U.S. PATENT DOCUMENTS

| | | | |
|---|---|---|---|
| 3,166,072 | 1/1965 | Sullivan, Jr. | 606/220 |
| 3,541,591 | 11/1970 | Hoegerman | 606/232 |
| 3,952,377 | 4/1976 | Morell . | |
| 4,060,089 | 11/1977 | Noiles | 606/220 |
| 4,461,059 | 7/1984 | Bury . | |
| 4,532,926 | 8/1985 | O'Holla . | |
| 4,534,350 | 8/1985 | Golden et al. | 606/220 |
| 4,573,469 | 3/1986 | Golden et al. . | |
| 4,644,953 | 2/1987 | Lahodny et al. . | |
| 4,724,839 | 2/1988 | Bedi et al. . | |
| 4,741,330 | 5/1988 | Hayhurst | 606/232 |
| 4,890,613 | 1/1990 | Golden et al. . | |
| 4,919,370 | 4/1990 | Martin et al. . | |
| 4,932,960 | 6/1990 | Green et al. . | |
| 5,059,206 | 10/1991 | Winters . | |
| 5,258,015 | 11/1993 | Li et al. | 24/453 |
| 5,306,290 | 4/1994 | Martins et al. . | |
| 5,370,661 | 12/1994 | Branch | 606/232 |

*Primary Examiner*—Michael Powell Buiz
*Assistant Examiner*—Mark S. Leonardo
*Attorney, Agent, or Firm*—McAulay Fisher Nissen Goldberg & Kiel, LLP

[57] ABSTRACT

A laparoscopic suturing method comprises the steps of (a) disposing a laparoscopic cannula in an abdominal wall of the patient, (b) moving a first end section of a suture through the laparoscopic cannula and into an abdominal cavity of the patient so that a second end section of the suture remains outside the patient, (c) passing the first end section of the suture through organic abdominal tissues of a patient, and (d) drawing the first end section of the suture back out through the laparoscopic cannula upon passing of the suture through the abdominal tissues of the patient. Upon drawing of the first end section of the suture out of the patient, a suture locking device is slid along the suture end sections and through the laparoscopic cannula until the locking device is substantially juxtaposed to the organic tissues at the opening. Then, the suture end sections are severed on a side of the locking device opposite the abdominal tissues and the opening. The locking device has a pair of channels with barbs pointed in one direction for preventing the suture end sections from being removed from the device.

26 Claims, 5 Drawing Sheets

LAPAROSCOPIC SUTURING TECHNIQUE AND ASSOCIATED DEVICE

CROSS-REFERENCE TO A RELATED APPLICATION

This application is a continuation-in-part of application Ser. No. 08/195,749 filed Feb. 10, 1994, now U.S. Pat. No. 5,391,173.

BACKGROUND OF THE INVENTION

This invention relates to a suture closure device for particular use in laparoscopic surgery. This invention also relates to a method for closing a suture, particularly in laparoscopic surgery.

Laparoscopic surgery is currently a rapidly spreading innovative medical technique. In laparoscopic surgery, internal organs of the patient are operated upon through a plurality of sleeves inserted in the abdominal wall of the patient. The progress of the operation is continuously monitored by the surgeon and assisting personnel with the aid of a specialized camera device called a laparoscope. The laparoscope is itself inserted into the patient through one of the sleeves in the abdominal wall. The action of the distal ends of laparoscopic instruments on the internal tissues of the patient is observed on one or more television monitors connected to the laparoscope.

One of the drawbacks of laparoscopic surgery is the inability to effectively form sutures. This problem is solved by the present invention.

OBJECTS OF THE INVENTION

An object of the present invention is to provide a new technique for forming sutures.

Another object of the present invention is to provide such a technique which can be used in laparoscopic surgery.

A further object of the present invention is to provide a device for use in quickly locking a suture.

A more particular object of the present invention is to provide such a device which can be used in laparoscopic operations.

Yet another object of the present invention is to provide an instrument for applying a suture closure device to a suture in laparoscopic surgery.

These and other objects of the present invention will be apparent from the drawings and detailed descriptions herein.

SUMMARY OF THE INVENTION

A device for locking a suture particularly during a laparoscopic surgical operation comprises, in accordance with the present invention, a body member made of biocompatible material and provided with a passageway for receiving a suture. The body member is further provided with locking compoentry or elements for preventing a suture from passing in a first predetermined direction along the passageway. The device has dimensions sufficiently small to enable insertion of the device into a patient's body via a laparoscopic cannula.

According to another feature of the present invention, the locking componentry is disposed along the passageway through the body member and allows the suture to slide relative to the body member in a second direction through the passageway opposite to the first direction. The locking componentry in this case may take the form of a plurality of barbs. The barbs extend at least partially radially inwardly and may be permanently angled in the second direction. Alternatively, if the barbs are flexible, they bend in the second direction upon an insertion of suture strands through the passageway in the second direction.

According to another feature of the present invention, the body member tapers down in the direction of slidability of a suture through the passageway. The passageway itself may be tapered in that direction.

The body member may take the form of a slotted ring provided with flared extensions at the slot for facilitating a lateral insertion of a suture into the ring.

The device described above is used to close or lock a suture. Upon a passing of the suture through organic tissues of a patient so that two strands of the suture extend from the organic tissues on opposite sides of an opening in the tissues, at least one of the strands is inserted into the passageway. The other strand is either pre-inserted through the device or is threaded through the device at this juncture. Then, the locking device is slid along the two strands until the locking device is substantially juxtaposed to the organic tissues at the opening in the organic tissues of the patient, thereby drawing the strands together and locking the strands in a tightened closure configuration. The strands are then severed on a side of the locking device opposite the organic tissues and the opening.

In one embodiment of the locking device in accordance with the present invention, the body member is provided with a pair of substantially parallel passageways or channels, each of the channels being provided with barbs or other locking elements for preventing a suture from passing in the first predetermined direction along the respective channel while allowing the suture to slide relative to the body member in the opposite direction through the respective channel. In that event, one suture strand or end section is inserted through one channel of the locking device and the other strand or end section is inserted through the other channel. It is possible, however, to provide the locking device with one channel or passageway, both strands of the suturing device being inserted through that passageway.

According to another feature of the present invention, the locking componentry on the body member of the suture locking device includes an element for wedging the suture in the passageway. The wedging element may be a conically tapered plug attached to the body member via a flexible link or strap. The plug is inserted into the passageway of the body member upon an insertion of suture strands through the passageway and a juxtaposition of the body member to the tissues being sutured.

In another specific embodiment of a suture locking device in accordance with the present invention the locking componentry includes a plurality of tapered slots provided on the body member for receiving the suture in a friction lock. In this case, the body member may be X-shaped with a pair of opposite tapered suture-receiving slots or W-shaped with a pair of substantially parallel suture-receiving slots. During a suturing operation, suture strands may be inserted into the slots at the tissues being sutured. Alternatively, the suture strands may be inserted into the slots outside of the patient, with the locking device being subsequently slid down the sutures through a laparoscopic cannula to the tissues inside the patient.

A laparoscopic suturing method in accordance with the present invention comprises the steps of (a) disposing a first and a second laparoscopic cannula in a skin surface of a patient, (b) moving at least one end section of a suture through the first laparoscopic cannula and into a body cavity of the patient, and (c) using a laparoscopic instrument to pass the end section of the suture through internal organic tissues of the patient, thereby defining two strands of the suture extending from the internal organic tissues of the patient. The method utilizes a locking device comprising a body member made of biocompatible material and provided with a passageway for receiving the suture, the body member being further provided with locking componentry for effectively preventing the suture from passing in a first predetermined direction along the passageway. The body member is of dimensions sufficiently small to enable insertion of the device into a patient's body via one of the laparoscopic cannulas. The method also comprises the steps of (d) inserting the locking device into the patient through the one of the laparoscopic cannulas, (e) manipulating the suture and the locking device so that the strands are connected to the locking device and so that at least one of the strands passes through the passageway and is locked thereto by the locking componentry, (f) positioning the locking device and the suture so that the locking device is substantially juxtaposed to the internal organic tissues, and (g) severing the suture strands on a side of the locking device opposite the internal organic tissues upon completion of the steps of inserting, manipulating and positioning.

Where the body member is a ring provided with a slot, the step of manipulating the suture and the locking device includes the step of inserting the one strand laterally through the slot so that the one strand traverses the ring.

Where the locking componentry includes a wedging element, the step of manipulating the suture and the locking device includes the step of actuating or manipulating the wedging element to lock the one strand to the locking device. The wedging element may take a frustoconical form, in which case actuating the wedging element includes the step of inserting that element at least partially through the passageway in the locking device.

The partial insertion of the wedging element into the ring may be performed upon positioning of the locking device and the suture so that the locking device is substantially juxtaposed to the internal organic tissues. In addition, the wedging element may be attached to the body member via a flexible link. Then the actuating step includes bending the flexible link to properly position the wedging element.

According to another feature of the present invention, the locking componentry on the locking device may be provided along the passageway for allowing the suture to slide relative to the body member in a second direction through the passageway opposite to the first direction. The positioning of the locking device next to the internal organic tissues of the patient then includes the step of sliding the locking device along at least the one of the strands.

According to another feature of the present invention, the step of manipulating the suture and the locking device includes the step of coupling the locking device to the one strand outside of the patient's body. In that event, the method further comprises the step of sliding the locking device along the one strand and through the first laparoscopic cannula.

The step of sliding the locking device along a suture strand through the first laparoscopic cannula may be implemented by inserting a distal end portion of an elongate instrument through the cannula, and pushing the locking device along the one strand by engaging the locking device with the distal end portion of the instrument.

Where the locking componentry includes a plurality of barb-like projections on the body member, the method may additionally comprise the step of bending the barb-like projections in an insertion of the one of the strands through the passageway during the step of manipulating.

As discussed above, the body member may be provided with a pair of substantially parallel channels, the passageway constituting one of the channels and each of the channels being provided with locking componentry for preventing a suture from passing in the first predetermined direction along the respective channel while allowing the suture to slide relative to the body member in the second direction through the respective channel. In that case, the step of manipulating the suture and the locking device includes the step of inserting the strands into respective ones of the passageways.

In one embodiment of the present invention, the passageway is one of a plurality of slots on the body member, while the locking componentry includes tapers of the slots provided on the body member for receiving the suture in a friction lock. In this embodiment of the invention, the step of manipulating the suture and the locking device includes the step of inserting the strands into respective ones of the slots so that the strands are wedged into the slots.

According to another feature of the present invention, the step of inserting the strands into the slots is performed outside of the patient's body, and the method further comprises the step of sliding the locking device along the strands and through the first laparoscopic cannula. As discussed above, the step of sliding the locking device along the suture strands through the first laparoscopic cannula may be implemented by inserting a distal end portion of an elongate instrument through the cannula, and pushing the locking device along the strands by engaging the locking device with the distal end portion of the instrument.

In another embodiment of the present invention, the insertion of the strands into the slots of the locking device is performed inside the patient with the aid of at least one laparoscopic instrument such as a laparoscopic graspers.

According to a further feature of the present invention, the step of manipulating the suture and the locking device includes the step of connecting the one strand to the locking device inside of the patient by using a laparoscopic instrument.

The step of manipulating the suture and the locking device generally includes the steps of connecting the strands to the locking device and locking the device. The step of connecting may be performed prior to the step of positioning and the step of locking after the step of positioning.

A surgical instrument for use in applying a locking device as described above to suture strands comprises an elongate instrument shaft insertable through a laparoscopic cannula, a holder or support at a distal end of the shaft for releasably holding the body member, and a closure component for engaging a locking part (cap, insert, conical section) of the suture locking device and moving the locking part to lock the suture device upon insertion of suture strands through the passageway in the body member. The closure means may include a pivoting or translating pusher member for wedging the locking element in the passageway.

Another laparoscopic instrument comprises, in accordance with the present invention, an elongate shaft, means at a distal end of the shaft defining an aperture, and a cutting edge attached to the instrument at the distal end along the aperture.

The present invention provides a device for use in quickly locking a suture. The device is especially useful in laparoscopic operations.

DETAILED DESCRIPTION

Figure 1:
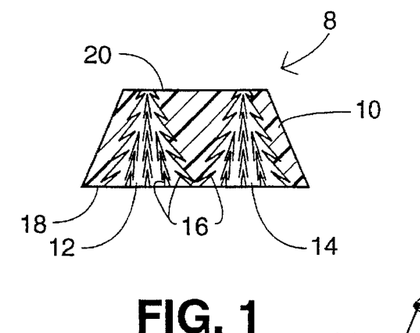
FIG. 1 is a schematic longitudinal cross-sectional view, on an enlarged scale, of a suture locking device in accordance with the present invention.

As illustrated in FIG. 1, a device 8 for locking a suture comprises a body member 10 made of biocompatible material and provided with two substantially parallel passageways or channels 12 and 14. Each passageway or channel 12 and 14 is lined with barb-like protuberances 16 pointed generally towards one end of the respective passageway 12 and 14. During use of locking device 8, a suture end (not shown in FIG. 1) is passed through a passageway 12 or 14 from one side 18 of device 8 towards an opposite side 20 thereof. Barb-like protuberances 16 serve to prevent the suture from moving in the opposite direction from side 20 to side 18, while allowing suture insertion in the opposite direction along the respective passageway. It is to be noted that device 8 may also work if just one passageway is provided (see FIGS. 7–9D).

As further illustrated in FIG. 1, body member 10 is tapered in a direction from side 18 to side 20. Likewise, passageways 12 and 14 each taper down in the same direction to facilitate insertion of a suture thread in the proper direction through the passageways.

Figure 2A:
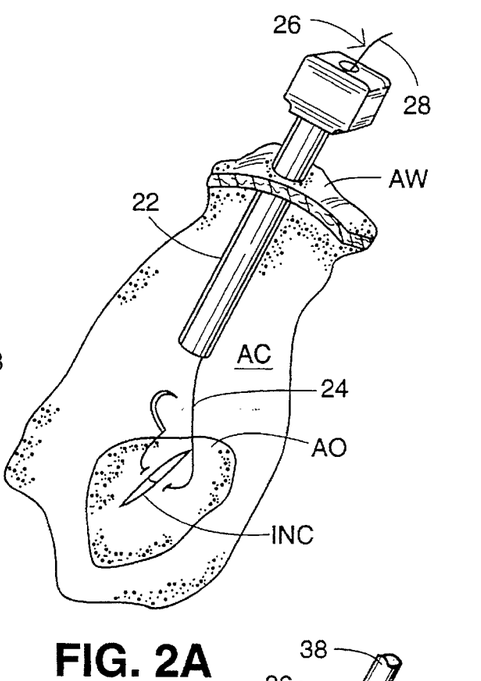
FIGS. 2A–2C are schematic cross-sectional views of a patient's abdomen, showing successive steps in a laparoscopic suturing procedure utilizing the device of FIG. 1.

As depicted in FIGS. 2A–2D, in a laparoscopic suturing procedure, a trocar sleeve or laparoscopic cannula 22 is disposed in an abdominal wall AW of the patient. A first end section or strand 24 of a suture 26 is moved through laparoscopic cannula 22 and into an abdominal cavity AC of the patient while a second end section or strand 28 of the suture remains outside the patient. As illustrated in FIG. 2A, first end section 24 of suture 26 is passed through tissues of an abdominal organ AO of the patient, for example, through the use of an arcuate needle as disclosed in U.S. Pat. No. 5,281,234, the disclosure of which is hereby incorporated by reference. More particularly, first end section 24 of suture 26 is passed through an incision INC in abdominal organ AO. Subsequently, first end section 24 is brought back out through laparoscopic cannula 22 (FIG. 2B) and passed through one passageway 12 or 14 of locking device 8.

Second end section 28 of suture 26 is inserted through the other passageway 14 or 12 of device 8, either before or after the passing of end section 24 therethrough. Alternatively, locking device 8 may be pre-attached to suture 26 along end section 28. In that case, only the first end section 24 need be threaded through device 8 during a laparoscopic operation.

Figure 2B:
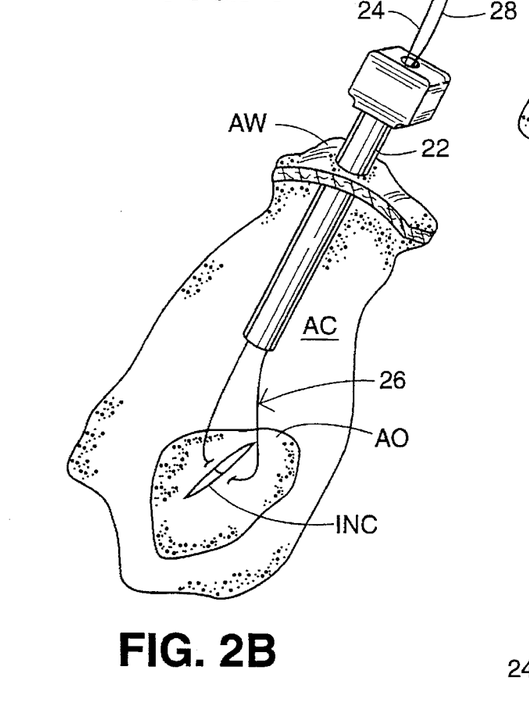
Figure 2C:
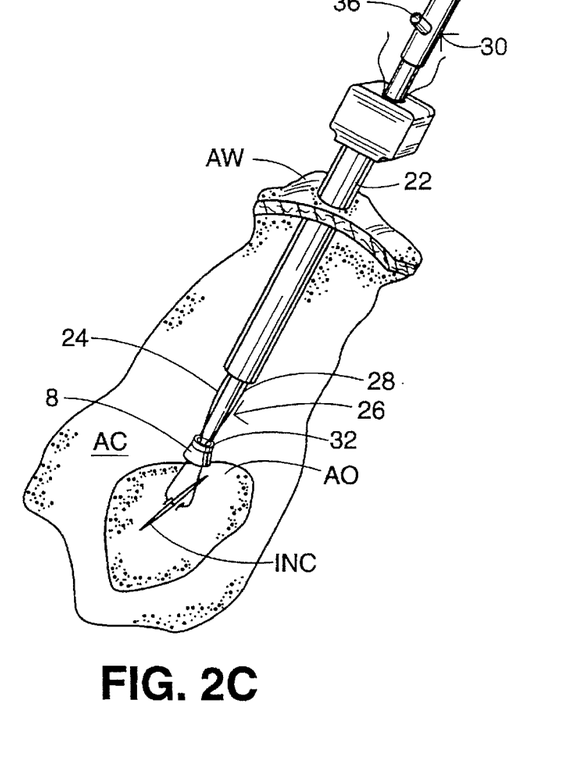
Figure 2D:
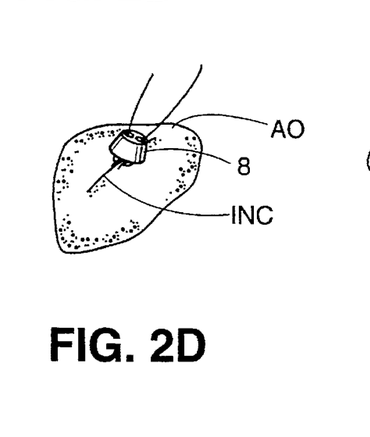
FIG. 2D is a schematic perspective view of an organ and an incision or wound closed by a suture which is locked by the device of FIG. 1, in accordance with the present invention.

As illustrated in FIG. 2B, both suture end sections or strands 24 and 28 are inserted through locking device 8 outside of the patient. Then, as depicted in FIG. 2C, an elongate laparoscopic instrument 30, provided at a distal end with a transversely extending ring 32 (see FIG. 3), is used to push locking device 8 along suture end sections 24 and 28 and through laparoscopic cannula 22 into abdominal cavity AC until the locking device is substantially juxtaposed to organ AO at incision or opening INC. Then, suture end sections 24 and 28 are severed on a proximal side of locking device 8, opposite abdominal organ AO and incision INC (FIG. 2D).

Figures 3, 4:
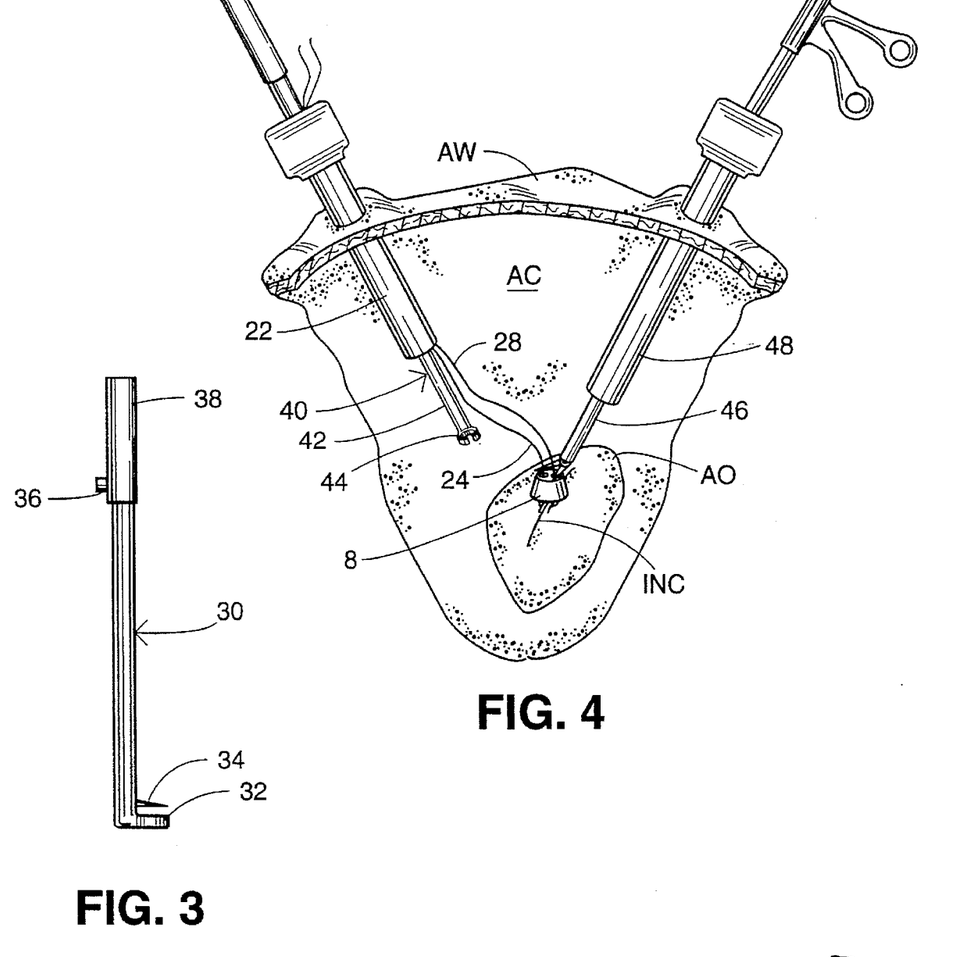
FIG. 3 is a side elevational view of a laparoscopic instrument shown in use in FIG. 2C, for applying the locking device of FIG. 1.
FIG. 4 is a schematic cross-sectional view similar to FIGS. 2A–2C, showing a step performable between the step of FIG. 2C and the step of FIG. 2D.
Figure 5:
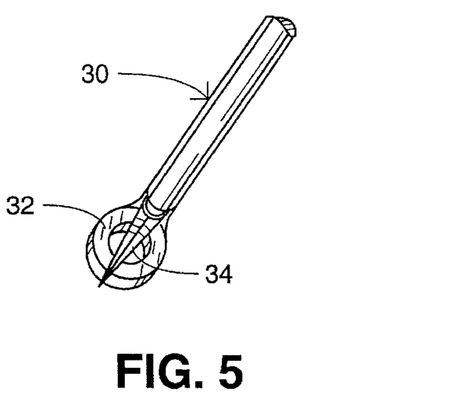
FIG. 5 is a partial schematic perspective view of the laparoscopic instrument of FIGS. 2C and 3, showing a cutting edge in accordance with the present invention.

In sliding locking device 8 along suture end sections 24 and 28, distal ring 32 of instrument 30 is inserted through laparoscopic cannula 22 and engages locking device 8 along the proximal side 20 thereof. As illustrated in FIGS. 3 and 5, pushing instrument 30 may be provided at a distal tip with a pair of scissors 34 or other movable cutting element which is operatively connected to an actuator button 36 on a handle 38 of the instrument. Upon a sliding of locking device 8 to the abdominal organ AO, button 36 is pressed to close the scissors or cutting element 34 to sever suture end sections 24 and 28. FIG. 5 shows scissors in a closed, cutting configuration. During a sliding of locking device 8 along suture end sections 24 and 28, scissors 34 are opened and spaced from the end sections 24 and 28.

In a modification of the above-described procedure, shown in FIG. 4, a pushing instrument 40 is used which has an elongate shaft 42 provided at a distal end with a slotted ring 44. Upon a juxtaposition of the locking device 8 with the abdominal organ AO under repair, instrument 40 is manipulated from outside the patient to remove suture end sections 24 and 28 from the ring (see FIG. 4). A laparoscopic scalpel or scissors 46 inserted into the abdomen through another trocar sleeve or laparoscopic cannula 48 is then operated to sever the suture end sections 24 and 28 at the proximal side of the locking device 8.

Figure 6:
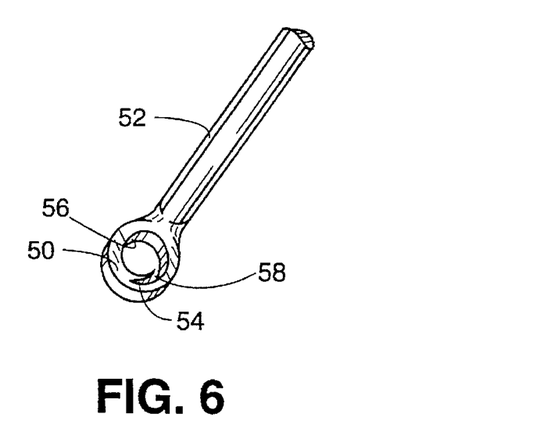
FIG. 6 is a partial schematic perspective view, showing a modification of the instrument of FIGS. 2C, 3, and 5.

As illustrated in FIG. 6, a guide ring 50 extending in a substantially transverse plane at the distal end of a laparoscopic instrument shaft 52 may be provided with a fixed cutting edge 54 which is reached by a suture only upon manipulating the suture and the instrument to pass the suture from a main guide aperture 56 and through a labyrinthine type slot 58. The labyrinthine slot 58 prevents inadvertant severing of a suture during an insertion of locking device 8.

It is to be noted that aperture 56 in the instrument of FIG. 6, as well as the corresponding guide apertures in other pushing instruments disclosed herein, is smaller than the proximal side 20 of locking device 8.

Figures 7, 8, 9A, 9B, 9C, 9D:
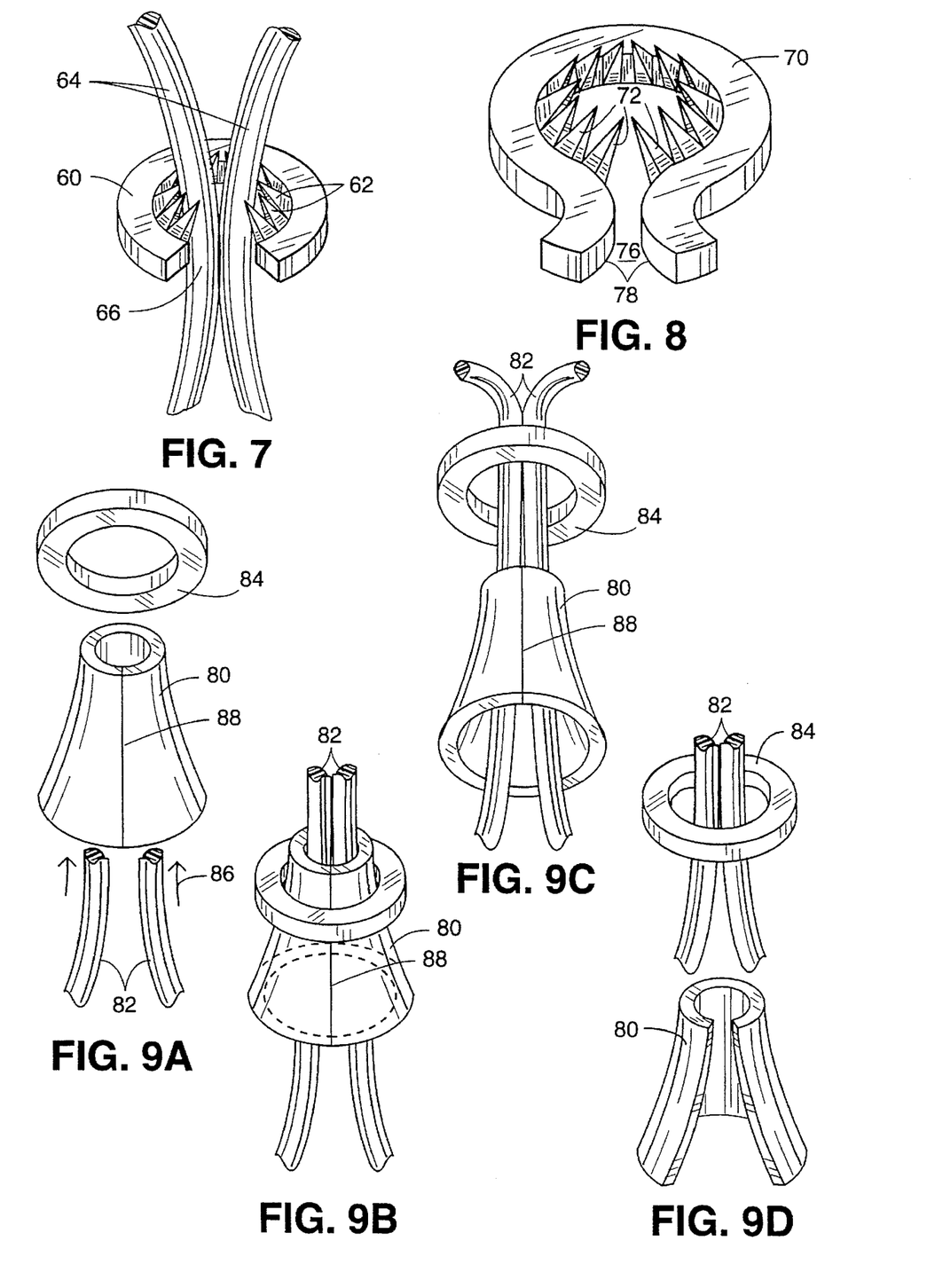
FIG. 7 is a schematic perspective view, on an enlarged scale, of another locking device in accordance with the present invention, showing two strands of a suture inserted through the locking device.
FIG. 8 is a schematic perspective view, on a substantially enlarged scale, of a further locking device in accordance with the present invention.
FIG. 9A is a schematic exploded perspective view of a suture locking device, suture strands and a suture threading device in accordance with the present invention.
FIG. 9B is a schematic perspective view of the suture locking device, suture strands and the suture threading device of FIG. 9B, showing the suture strands inserted through the threading device which in turn is inserted through the locking device.
FIG. 9C shows a step in a suture insertion operation subsequent to a step shown in FIG. 9B.
FIG. 9D shows another succeeding step in a suture insertion operation subsequent to the step shown in FIG. 9C.

As illustrated in FIG. 7, another locking device utilizable with the method discussed above with reference to FIGS. 2A–2D and 4 takes the form of a ring 60 provided along an inner side with barbs 62 inclined in a common axial direction for purposes of preventing suture strands 64 from sliding relative to ring 60 in a direction opposite to the direction of inclination of barbs 62. Ring 62 is optionally provided with a slot 66 for enabling a lateral insertion of strands 64 into ring 62. Barbs or projections 62 are angularly spaced from one another and extend at least partially radially inwardly from ring 60. Barbs or projections 62 may be flexible so as to move from a planar array (not shown) to the array angled in one direction, as shown in FIG. 7, upon the insertion of suture strands 64 through the device.

FIG. 8 shows a further locking device in the form of a ring 70 provided along an inner side with barbs 72 inclined in a common axial direction for purposes of preventing suture strands (not shown) from sliding relative to ring 70 in a direction opposite to the direction of inclination of barbs 72. Ring 72 is also provided with a slot 76 for enabling a lateral insertion of suture strands into ring 72. To further facilitate the insertion of a suture into ring 72, the ring is provided on opposite sides of slot 76 with outwardly flared lips or extensions 78. Barbs or projections 72 are angularly spaced from one another and extend at least partially radially inwardly from ring 70. Barbs or projections 72 may be flexible so as to move from a planar array (not shown) to the array angled in one direction, as shown in FIG. 7, upon the insertion of suture strands through the device.

As depicted in FIG. 9A, a substantially conical threading or guiding device 80 is provided for facilitating insertion of suture strands 82 through an annular suture locking device 84. Suture strands 82 are inserted in the direction of arrows 86 into threading device 80 upon an insertion of a tapered end of that device into locking device 84, as illustrated in FIG. 9B. Subsequently, after threading of suture strands 82 completely through device 80, the threading device is removed from locking device 84, as illustrated in FIG. 9C. The threading device 80 is provided with a slot 88, whereby that device may be opened to enable removal from suture strands 82, as shown in FIG. 9D. Locking device 84 is provided with non-illustrated barbs. Threading device 80 is made, at least along an outer surface, of a material which resists penetration by the barbs of locking device 84, thereby enabling withdrawal of the threading device 80 from locking device 84.

Figure 10:
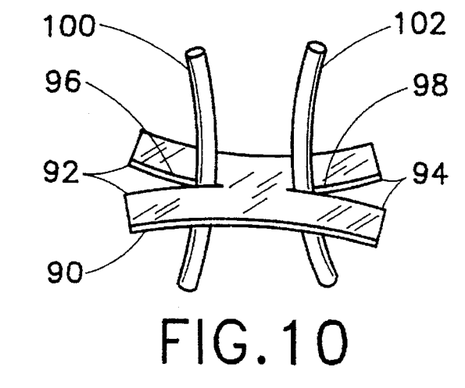
FIG. 10 is a schematic perspective view of another suture locking device in accordance with the present invention.

As shown in FIG. 10, another suture locking device comprises an X-shaped body member 90 with pairs of legs 92 and 94 defining a pair of opposing passageways 96 and 98 in the form of tapering slots which receive respective strands 100 and 102. Tapered slots 96 and 98 receive suture strands 100 and 102 in a friction lock. Suture strands 100 and 102 may be inserted, via the use of laparoscopic graspers, into slots 96 and 98 at the internal tissues being sutured. Alternatively, suture strands 100 and 102 may be inserted into slots 96 and 98 outside of the patient, with the locking device being subsequently slid down suture strands through a laparoscopic cannula to the tissues inside the patient. Like other suture locking devices disclosed herein, body member 90 has dimensions sufficiently small to permit the insertion of the locking device into a patient via a laparoscopic cannula. Where body member 90 is attached to suture strands 100 and 102 outside of the patient, the locking device is inserted into the patient through the same laparoscopic cannula as the suture strands. Where body member 90 is attached to suture strands 100 and 102 inside of the patient, the locking device may be inserted into the patient via a different laparoscopic cannula or trocar sleeve.

Figure 11:
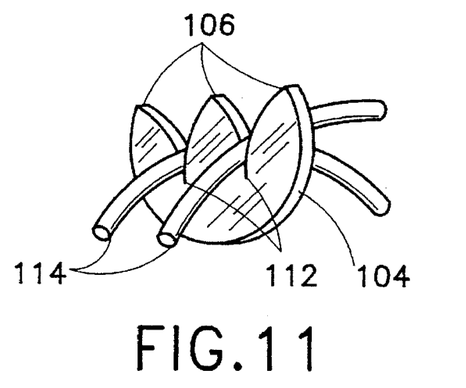
FIG. 11 is a schematic perspective view of a further suture locking device in accordance with the present invention.

A similar suture locking device is illustrated in FIG. 11. A generally W-shaped body member 104 has three generally parallel leg formations 106 defining two substantially parallel tapered slots 112 acting as passageways for receiving respective suture strands 114 in a suture locking procedure during a surgical operation. Slots 112 are tapered to receive suture strands 114 in a friction lock. Suture strands 114 may be inserted, via the use of laparoscopic graspers, into slots 112 at the internal tissues being sutured. Alternatively, suture strands 114 may be inserted into slots 112 outside of the patient, with the locking device being subsequently slid down suture strands through a laparoscopic cannula to the tissues inside the patient.

Figure 12A:
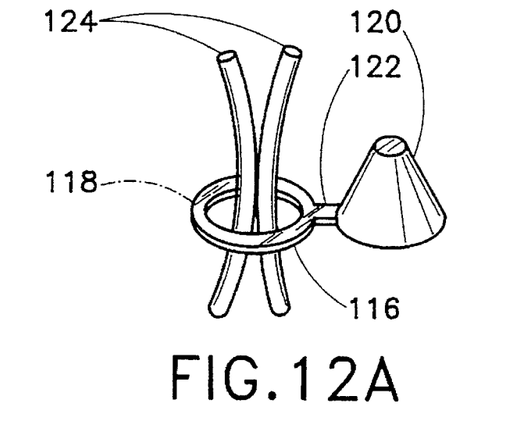
FIG. 12A is a schematic perspective view of yet another suture locking device in accordance with the present invention, showing the device in an opened, pre-use configuration.
Figure 12B:
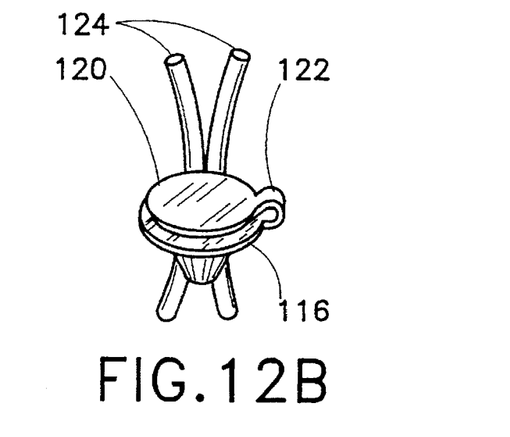
FIG. 12B is a schematic perspective view of the suture locking device of FIG. 12B, showing the device in a closed, use configuration.

As illustrated in FIGS. 12A and 12B, another suture locking device includes a ring 116 which is optionally formed with a slot 118 for sideways or lateral insertion of suture strands 124 into a passageway (not designated) defined by the ring. A tapered locking component in the form of a frustoconical section or plug 120 is attached to ring 116 via a flexible strap or tie element 122. Upon a disposition of suture strands 124 so that they traverse ring 116, as shown in FIG. 12A, frustoconical section 120 is maneuvered, by bending strap 122, and wedged partially into ring 116, thereby crimping suture strands to ring 116, as shown in FIG. 12B. Generally, it is contemplated that frustoconical section 120 is partially inserted into ring 116 upon a justaposition of the ring to internal organic tissues of the patient to be sutured.

Figure 13:
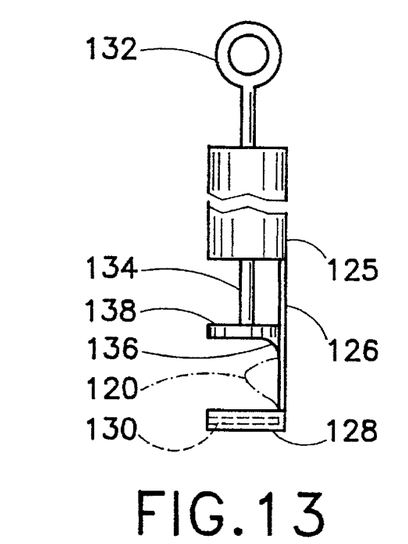
FIG. 13 is a schematic side elevational view of a laparoscopic instrument for applying the locking device of FIGS. 12A and 12B.

As depicted in FIG. 13, the suture locking device of FIGS. 12A and 12B may be employed, during a laparoscopic surgical operation, with the aid of an elongate instrument having a main shaft 125 provided at a distal end with a longitudinal extension 126 in turn formed at a distal end with a transversely extending foot or flange 128. Foot or flange 128 is provided with a groove 130 for seating ring 116. Groove 130 may be formed as a shoulder (not illustrated) on a proximal side of foot or flange 128 or, alternatively, as a slot accessible laterally via an opening in a side of foot or flange 128.

At the onset of a suture closure procedure, ring 116 is seated in groove 130, while conical section 120 is oriented at a 90° angle, supported by extension 126, as shown in FIG. 13. A distal end portion of the instrument is then inserted into a patient's body via a laparoscopic cannula. Suture strands (not shown in FIG. 13) are drawn through ring 116 by laparoscopic graspers (not shown). An actuator handle 132 of a plunger member 134 is then pushed in a distal direction to close the suture locking device. More specifically, a camming protuberance 136 at the distal end of plunger member 134 separates conical section 120 from extension 126 during a distally directed stroke of the plunger member. Continued motion of plunger member 134 in the distal direction turns conical section 120 from the 90° orientation shown in FIG. 13 to a 180° orientation shown in FIG. 12B and causes a pusher element 138 at the distal end of plunger member 134 to wedge conical section 120 into ring 116, thereby binding the suture strands.

Other equivalent designs for the locking instrument of FIG. 13 will occur to those skilled in the art. For example, foot or flange 128 may include a pair of substantially C-shaped jaws for temporarily clamping ring 116 during a suture closure procedure. The insertion of conical section 120 into ring 116 may be implemented by a pivoting pusher (not shown) rather than by translating pusher element 138. Essential functions of the instrument include holding ring 116 and pivoting conical section 120 to wedge it into ring 116.

Figure 14:
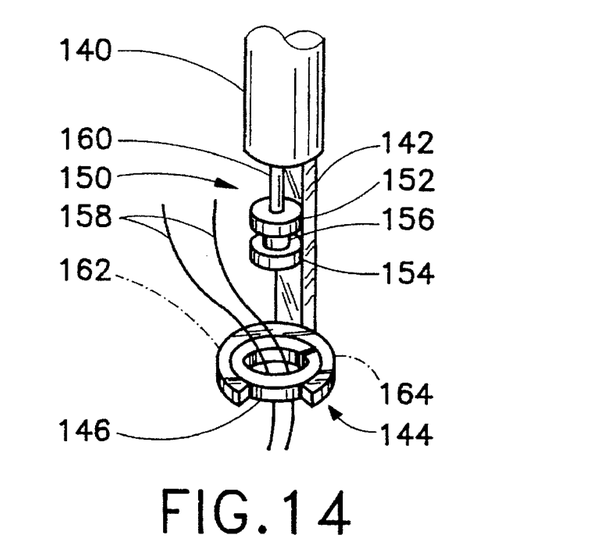
FIG. 14 is a schematic perspective view of another laparoscopic instrument in accordance with the present invention for applying yet another suture locking device shown in FIG. 14.

As depicted in FIG. 14, another laparoscopic instrument for effectuating the closure of a suture by a locking device during a laparoscopic surgical operation comprises a main shaft 140 provided at a distal end with a longitudinal extension 142 in turn formed at a distal end with a transversely extending foot or flange 144. Foot or flange 144 may be provided with a groove, shoulder or slot (not illustrated) for seating a ring 146 of a two-piece suture locking device 148. The other piece of the suture locking device is a snap-in insert 150 including a pair of flanges 152 and 154 connected by a midsection 156 of reduced diameter. Ring 146 defines a passageway (not designated) for receiving suture strands 158 and midsection 156 of snap-in insert 150.

At the onset of a suture closure procedure, ring 146 is held in foot or flange 144. Foot or flange 144 may be resilient for facilitating insertion of ring 146 at the beginning of a suture closure procedure and for facilitating removal of ring 146 and snap-in insert 150 at the end of the procedure. A distal end portion of the instrument of FIG. 14 is then inserted into a patient's body via a laparoscopic cannula. Suture strands 158 are drawn through ring 146 by laparoscopic graspers (not shown). A plunger member 160 releasably bearing snap-in-insert 150 as shown in FIG. 14 is then pushed in a distal direction to close the suture locking device. More specifically, plunger member 160 forces distal flange 154 of snap-in insert 150 through ring 146, thereby capturing suture strands 158.

Other equivalent designs for the locking instrument of FIG. 14 will occur to those skilled in the art. For example, foot or flange 144 may include a pair of substantially C-shaped jaws 162 and 164 for temporarily clamping ring 146 during a suture closure procedure. The insertion of snap-in insert 150 into ring 146 may be implemented by a pivoting pusher (not shown) rather than by translating plunger member 160. Both plunger member 160 and the pivoting pusher may be provided with a knob (not shown) releasably inserted into a recess (not designated) in snap-in insert 150. Essential functions of the instrument of FIG. 14 include holding ring 146 and pushing flange 154 of snap-in insert 150 through the ring to lock the suture strands 158.

Figures 15A, 15B, 16, 17:
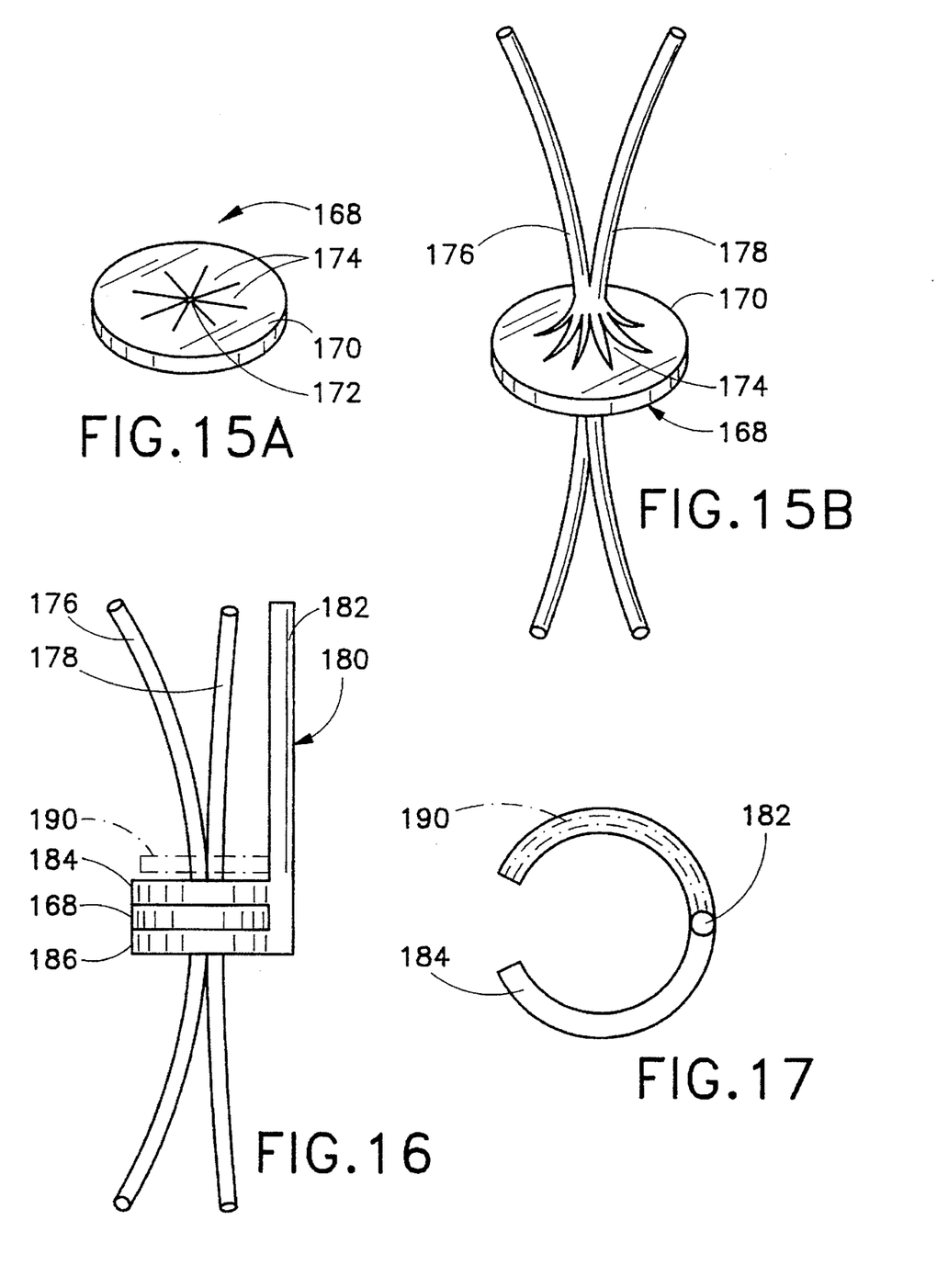
FIG. 15A is a schematic perspective view of another suture locking device in accordance with the present invention, showing the device prior to use.
FIG. 15B is a schematic perspective view of the suture locking device of FIG. 15A, showing the device in use with a pair of suture strands.
FIG. 16 is a schematic side elevational view of a laparoscopic instrument assembly for employing the suture locking device of FIGS. 15A and 15B.
FIG. 17 is a schematic top view of the portion of the laparoscopic instrument assembly of FIG. 16.

FIGS. 15A and 15B illustrate a modification of the suture locking device of FIG. 1. A device 168 for locking a suture comprises a body member 170 made of biocompatible material and provided with a single passageway or channel 172 defined by a plurality of radially inwardly oriented barb-like protuberances 174. During use of locking device 168, suture strands 176 and 178 are passed through passageway 172 from one side of device 168 towards an opposite side thereof. Generally, this insertion step occurs outside the patient, with the locking device 168 being slid along the suture strand into the patient through a laparoscopic cannula. Barb-like protuberances 174 are resilient and bend during the insertion of the suture strands 176 and 178 through passageway 172, as illustrated in FIG. 15B. Barb-like protuberances 174 serve to prevent the suture from moving relative to body member 170 in a direction opposite to the direction of strand insertion, while allowing relative motion in the suture insertion direction. The suture locking device 168 of FIGS. 15A and 15B is used in basically the same way as the suture locking device of FIG. 1.

As illustrated in FIGS. 16 and 17, a laparoscopic instrument 180 for assisting in the employment of the locking device 168 of FIGS. 15A and 15B comprises an elongate instrument shaft 182 provided at a distal end with a pair of axially spaced C-shaped brackets or flanges 184 and 186. With both strands 176 and 178 extending outside of the patient (compare FIG. 2B), the locking device 168 with strands 176 and 178 is inserted between flanges 184 and 186, as shown in FIG. 16. A distal end portion of instrument 180 including flanges 184 and 186 and locking device 168 is inserted into the patient via a laparoscopic cannula. During this procedure, locking device 168 is slid along strands 176 and 178. Upon juxtaposition of flange 186 and internal organic tissues of the patient, an arcuate blade 190 disposed along a proximal side of flange 184 is pivoted about shaft 182, thereby severing suture strands 176 and 178 at locking device 168.

It is to be understood that the procedures, suture locking devices, and laparoscopic instruments described herein may be used in various kinds of laparoscopic surgery such as thorasic and abdominal surgery.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are profferred by way of example to facilitate comprehension of the invention and should not be construed to limit the scope thereof.

What is claimed is:

1. A laparoscopic surgical closure method comprising the steps of:

disposing a first and a second laparoscopic cannula in a skin surface of a patient;

moving at least one end section of a suture through said first laparoscopic cannula and into a body cavity of the patient;

upon completion of said step of moving, using a laparoscopic instrument to pass said end section of said suture around internal organic tissues of the patient, thereby defining two strands of said suture extending from the internal organic tissues of the patient;

providing a locking device comprising a body member made of biocompatible material and provided with a passageway for receiving said suture, said body member being further provided with locking means for effectively preventing said suture from passing in a first predetermined direction along said passageway, said body member being of dimensions sufficiently small to enable insertion of the device into a patient's body via one of said first and said second laparoscopic cannula;

inserting said locking device into the patient through said one of said first and said second laparoscopic cannula;

manipulating said suture and said locking device so that said strands are connected to said locking device and so that at least one of said strands passes through said passageway and is locked thereto by said locking means;

positioning said locking device and said suture so that said locking device is substantially juxtaposed to said internal organic tissues; and upon completion of said steps of inserting, manipulating and positioning, severing said strands on a side of said locking device opposite said internal organic tissues.

2. The method defined in claim 1 wherein said locking means is provided along said passageway and allows the suture to slide relative to said body member in a second direction through said passageway opposite to said first direction, said step of positioning including the step of sliding said locking device along at least said one of said strands.

3. The method defined in claim 2 wherein said step of manipulating includes the step of coupling said locking device to said one of said strands outside of the patient's body, further comprising the step of sliding said locking device along said one of said strands and through said first laparoscopic cannula.

4. The method defined in claim 2 wherein said body member is provided with a pair of substantially parallel channels, said passageway constituting one of said channels, each of said channels being provided with locking means for preventing a suture from passing in said first predetermined direction along the respective channel while allowing the suture to slide relative to said body member in said second direction through the respective channel, said step of manipulating including the step of inserting said strands into respective ones of said passageways.

5. The method defined in claim 2 wherein said step of sliding includes the steps of:

providing an elongate instrument;

inserting a distal end portion of said elongate instrument through said first laparoscopic cannula; and pushing said locking device along said one of said strands by engaging said locking device with said distal end portion of said instrument.

6. The method defined in claim 1 wherein said body member is a ring provided with a slot, said step of manipulating including the step of inserting said one of said strands laterally through said slot so that said one of said strands traverses said ring.

7. The method defined in claim 1 wherein said locking means includes means for wedging said suture in said passageway, said step of manipulating including the step of actuating said means for wedging to lock said one of said strands to said locking device.

8. The method defined in claim 7 wherein said means for wedging includes a tapered element, said step of actuating including the step of inserting said tapered element at least partially through said passageway.

9. The method defined in claim 8 wherein said step of actuating is performed upon positioning of said locking device and said suture so that said locking device is substantially juxtaposed to said internal organic tissues.

10. The method defined in claim 7 wherein said means for wedging is attached to said body member via a flexible link, said step of actuating including the step of bending said flexible link to properly position said means for wedging.

11. The method defined in claim 1 wherein said passageway is one of a plurality of slots on said body member, said locking means including tapers of said slots provided on said body member for receiving said suture in a friction lock, said step of manipulating including the step of inserting said strands into respective ones of said slots so that said strands are wedged into said slots.

12. The method defined in claim 11 wherein said step of inserting said strands into said slots is performed outside of the patient's body, further comprising the step of sliding said locking device along said strands and through said first laparoscopic cannula.

13. The method defined in claim 12 wherein said step of sliding includes the steps of:

providing an elongate instrument;

inserting a distal end portion of said elongate instrument through said first laparoscopic cannula; and pushing said locking device along said strands by engaging said locking device with said distal end portion of said instrument.

14. The method defined in claim 11 wherein said step of inserting said strands into said slots is performed inside the patient with the aid of at least one laparoscopic instrument.

15. The method defined in claim 1 wherein said step of manipulating includes the step of connecting said one of said strands to said locking device outside of the patient, said step of inserting said locking device into the patient including the step of sliding said locking device along said one of said strands into the patient through said first laparoscopic cannula upon completion of said step of connecting.

16. The method defined in claim 1 wherein said step of manipulating includes the step of connecting said one of said strands to said locking device inside of the patient by using a laparoscopic instrument.

17. The method defined in claim 1 wherein said step of manipulating includes the steps of connecting said strands to said locking device and locking said device.

18. The method defined in claim 17 wherein said step of connecting is performed prior to said step of positioning and said step of locking is performed after said step of positioning.

19. A surgical instrument for use in laparoscopic surgery to apply a suture locking device to a suture wherein said suture locking device includes a body member made of biocompatible material end provided with a passageway for receiving a suture, said suture locking device further including locking means for preventing a suture from passing in a first predetermined direction along said passageway, said body member and said locking means being of dimensions sufficiently small to enable insertion of the device into a patient's body via a laparoscopic cannula, said instrument comprising:

an elongate instrument shaft insertable through a laparoscopic cannula;

means at a distal end of said shaft for releasably holding said body member; and closure means coupled to said instrument shaft for engaging said locking means and moving said locking means to lock the suture device upon insertion of suture strands through said passageway in said body member.

20. The instrument defined in claim 19 wherein said locking means includes a locking element insertable into said passageway, said closure means including a pusher member for wedging said locking element in said passageway.

21. The instrument defined in claim 20 wherein said pusher member translates relative to said shaft.

22. A device for locking a suture, particularly for locking a suture formed during a laparoscopic surgical operation, comprising a ring-shaped body member made of biocompatible material and provided with a passageway for receiving a suture, said passageway being substantially wider than a diameter of said suture, said body member being further provided with a tapered locking element insertable into said passageway for preventing a suture from passing in a first predetermined direction along said passageway, said locking element being attached to said body member via a flexible link, said body member and said locking element being of dimensions sufficiently small to enable insertion of the device into a patient's body via a laparoscopic cannula.

23. The device defined in claim 22 wherein said ring shaped-body member is a slotted ring.

24. The device defined in claim 22 wherein said passageway lies in a plane and has an axis, said locking element being insertable into said passageway along said axis substantially perpendicularly to said plane.

25. A device for locking a suture, particularly for locking a suture formed during a laparoscopic surgical operation, comprising an X-shaped body member made of biocompatible material and having two pairs of legs extending from a center of said body member in substantially opposite directions so as to define a two tapered slots for grippingly receiving a suture, said slots being open along a periphery of said device and tapering down toward said center, whereby said suture can be inserted into said slots solely by a relative lateral motion of said suture into said slots from said periphery, said tapered body member being of dimensions sufficiently small to enable insertion of the device into a patient's body via a laparoscopic cannula.

26. A device for locking a suture, particularly for locking a suture formed during a laparoscopic surgical operation, comprising a W-shaped body member made of biocompatible material and having three essentially co-planar legs extending from one side of said body member in a substantially common direction so as to define two tapered slots for grippingly receiving a suture, said slots being open along a periphery of said device and tapering down in a direction away from said periphery, whereby said suture can be inserted into said slots solely by a relative lateral motion of said suture into said slots from said periphery, said tapered body member being of dimensions sufficiently small to enable insertion of the device into a patient's body via a laparoscopic cannula.

* * * * *